(12) United States Patent
Tamura et al.

(10) Patent No.: US 6,533,913 B1
(45) Date of Patent: Mar. 18, 2003

(54) ELECTROPHORESIS METHOD, ELECTROPHORESIS DEVICE, AND MARKER SAMPLE USED FOR THE SAME

(75) Inventors: Takuro Tamura, Kanagawa (JP); Toshimasa Watanabe, Kanagawa (JP); Kenji Yamamoto, Kanagawa (JP); Toshiaki Ito, Kanagawa (JP); Junji Yoshii, Kanagawa (JP)

(73) Assignee: Hitachi Software Engineering, Co., Ltd., Kanagawa (JP)

( * ) Notice: Subject to any disclaimer, the term of this patent is extended or adjusted under 35 U.S.C. 154(b) by 0 days.

(21) Appl. No.: 09/452,854

(22) Filed: Dec. 2, 1999

(30) Foreign Application Priority Data

Dec. 4, 1998 (JP) .......................................... 10-345476

(51) Int. Cl.[7] .............................................. G01N 27/26
(52) U.S. Cl. ........................................................ 204/461
(58) Field of Search ................................ 204/450, 451, 204/452, 456, 461, 466, 600, 601, 603, 606, 612, 616; 356/344

(56) References Cited

U.S. PATENT DOCUMENTS

| 5,221,454 A | * | 6/1993 | Manian et al. ............... 204/612 |
| 5,525,516 A | * | 6/1996 | Krutak et al. ................. 436/56 |
| 5,677,196 A | * | 10/1997 | Herron et al. ............... 436/518 |

FOREIGN PATENT DOCUMENTS

JP 405322770 A * 12/1993

OTHER PUBLICATIONS

JAPIO abstract of Ono et al. (JP405322770A).*

* cited by examiner

*Primary Examiner*—Jill Warden
*Assistant Examiner*—Alex Noguerola
(74) *Attorney, Agent, or Firm*—Fish & Richardson P.C.

(57) ABSTRACT

An electrophoresis method, comprising simultaneously electrophoresing a test sample containing a plurality of molecules labeled with a plurality of luminescent reagents and a marker sample containing a plurality of molecules with known molecular weights labeled with the same plurality of luminescent reagents.

12 Claims, 12 Drawing Sheets

(1 of 12 Drawing Sheet(s) Filed in Color)

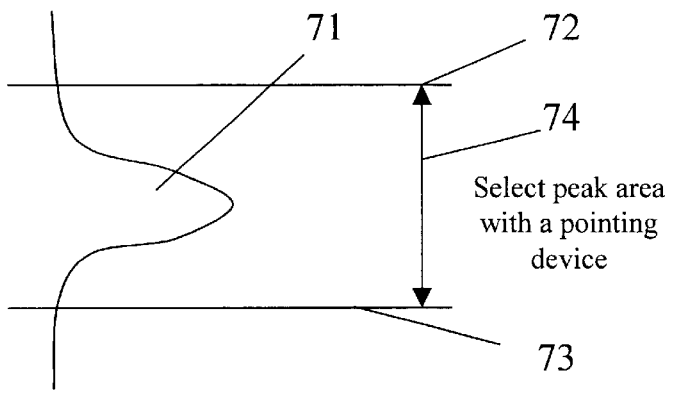
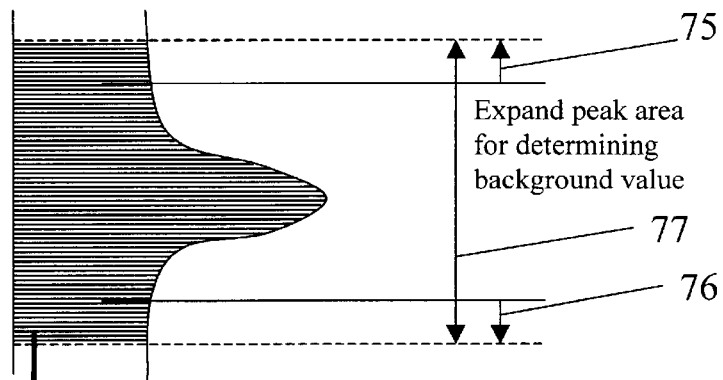
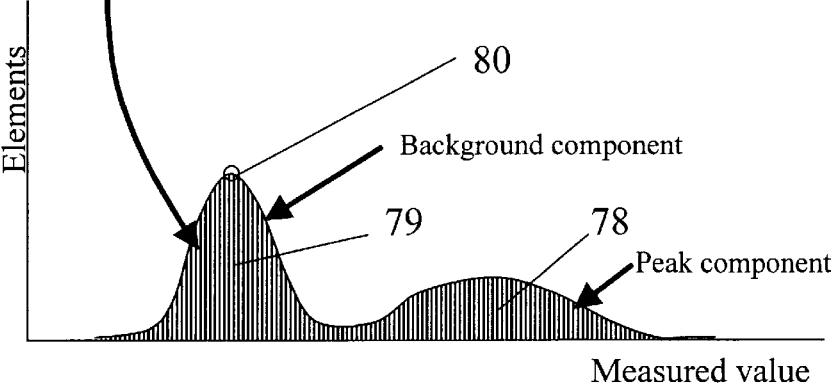

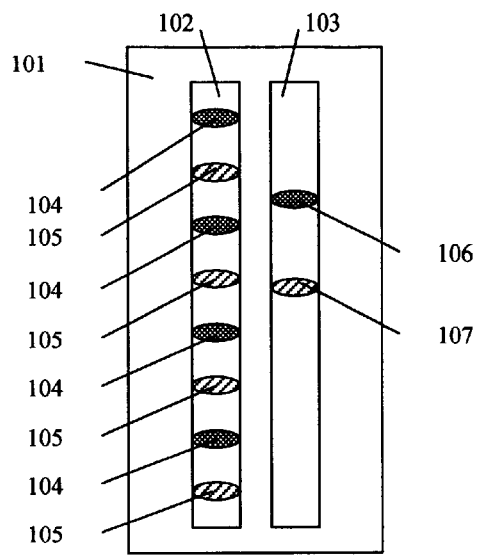
Fig. 7A
Locations of labeled molecules upon slab gel electrophoresis
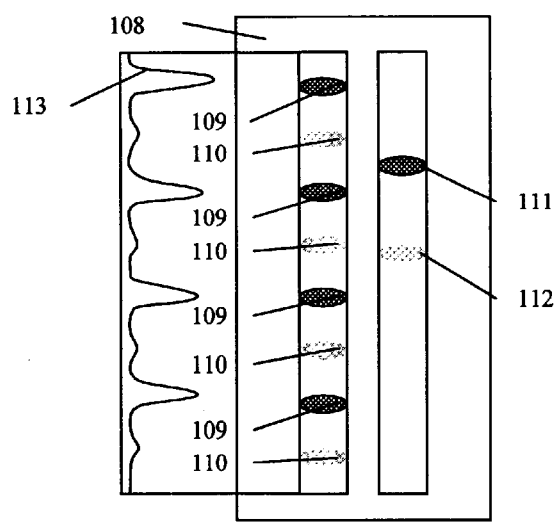
Fig. 7B Detection with optical filter a
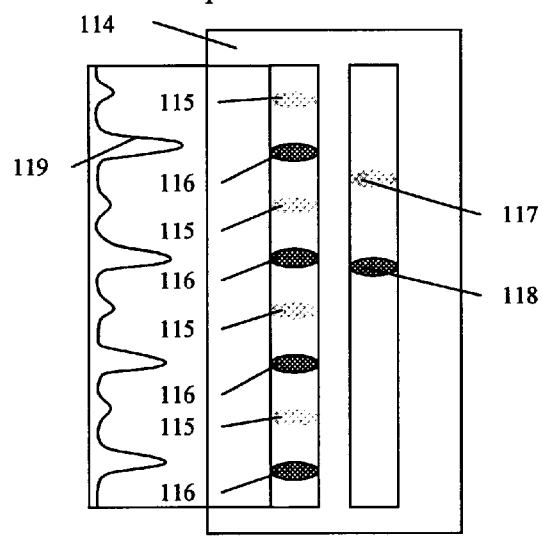
Fig. 7C Detection with optical filter b

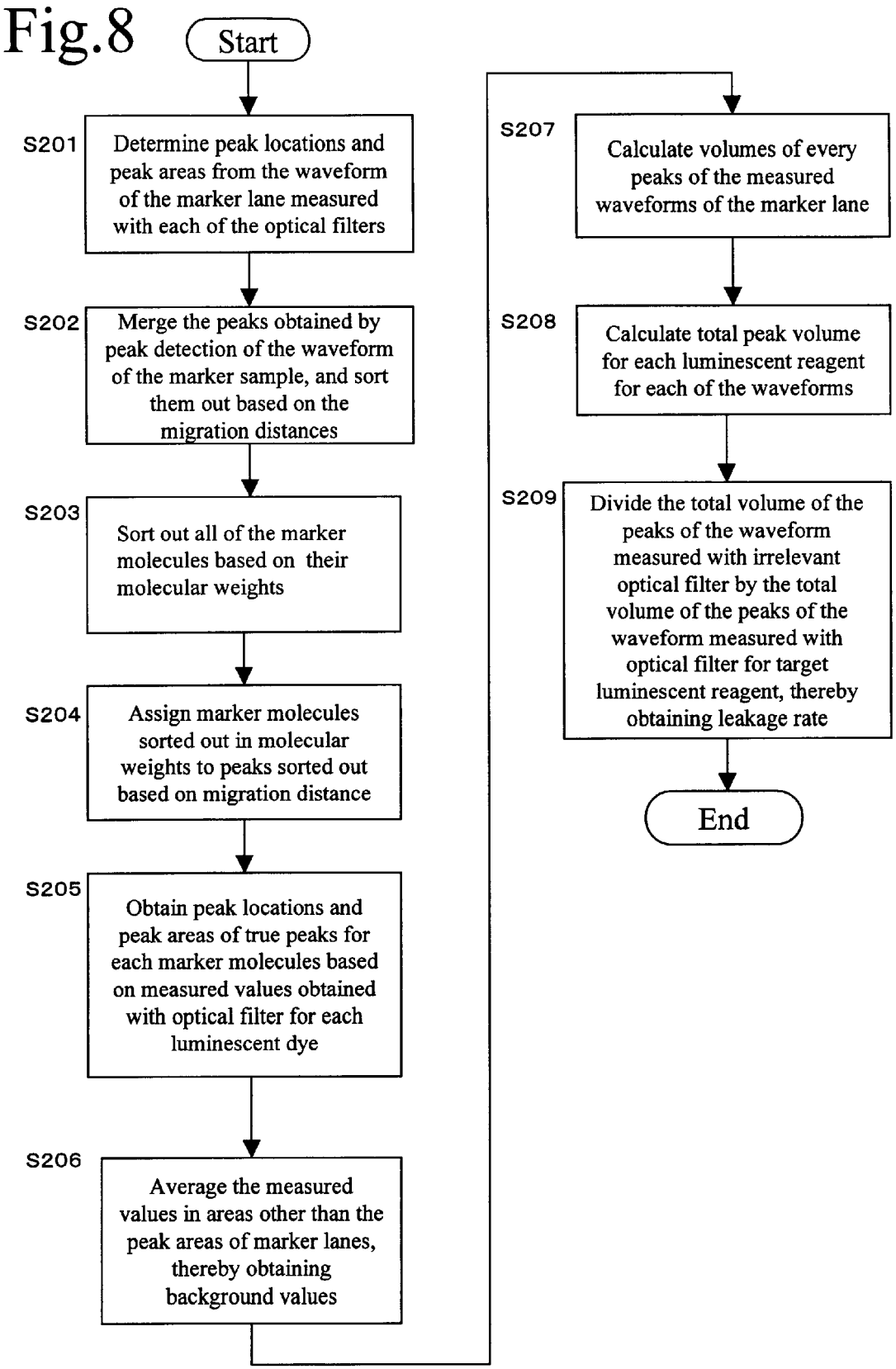

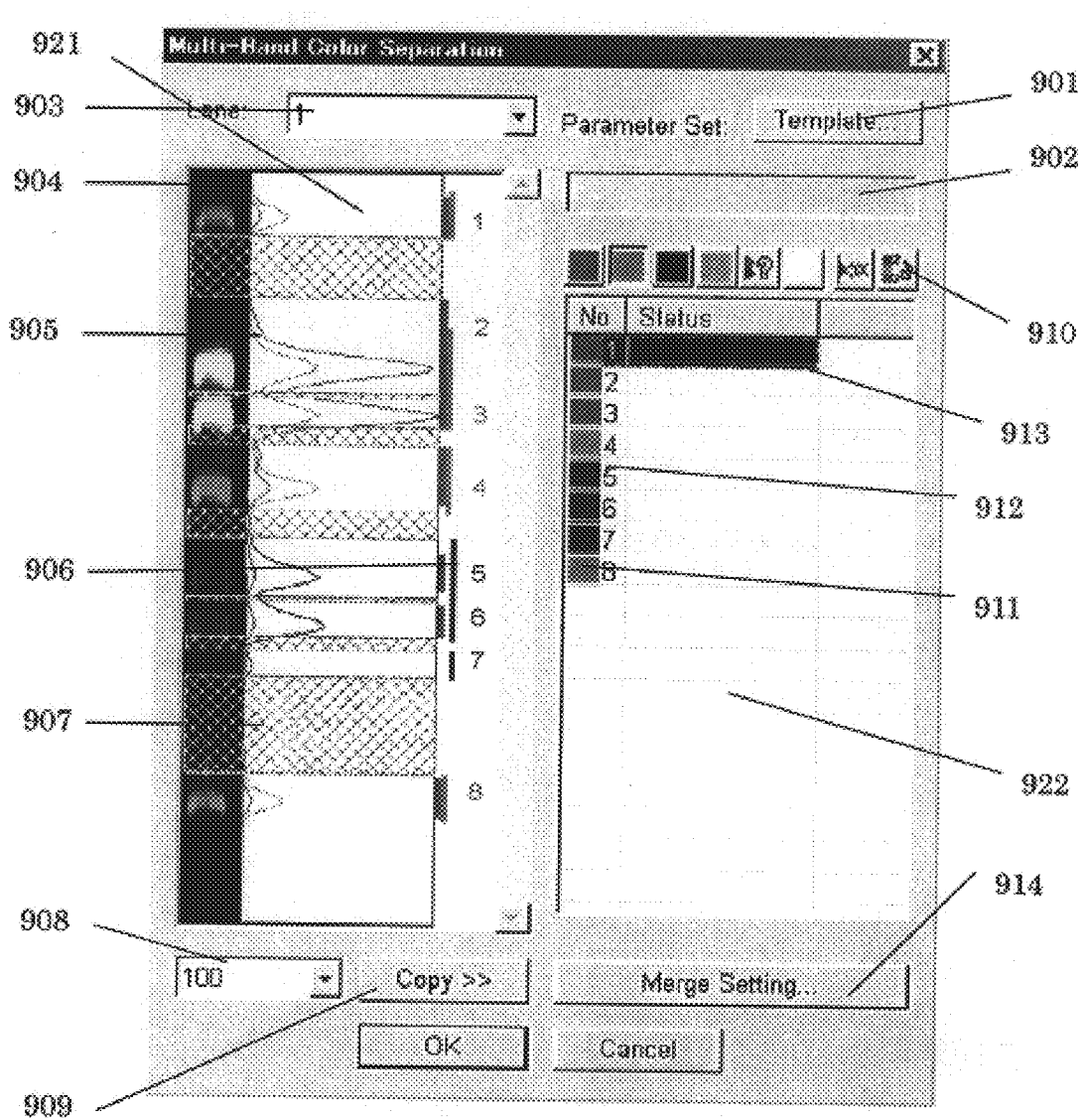

ELECTROPHORESIS METHOD, ELECTROPHORESIS DEVICE, AND MARKER SAMPLE USED FOR THE SAME

The present application under 35 USC §119 claims the benefit of the foreign priority application filed in Japan, serial number 345476/1998, filed Dec. 4, 1998. This application is explicitly incorporated herein by reference in its entirety and for all purposes.

FIELD OF THE INVENTION

The present invention relates to an electrophoresis method, an electrophoresis device, and a marker sample used for the same. More particularly, the present invention relates to an electrophoresis method and an electrophoresis device for separating and detecting a sample labeled with two or more luminescent reagents having different luminescent wavelength ranges, and to a marker sample used for such method and device.

BACKGROUND OF THE INVENTION

Various devices for detecting a sample by utilizing luminous phenomenon (e.g., fluorescence, chemiluminescence and fluorescent chemiluminescence) are known, such as a fluorescence measuring device, a chemiluminescence measuring device, an electrophoresis device and a biochip reading device. When such devices are used to determine a sample labeled with two or more luminescent reagents with different luminescent wavelength ranges, optical interference filters having high wavelength range selectivities are used for color separation. However, if the wavelength ranges of the luminescent reagents, even partially, overlap each other, a light component of an untargeted luminescent reagent passes through the optical filter, causing leak that needs to be excluded for the subsequent evaluation.

FIG. 1 is a schematic view showing an exemplary device for detecting a sample 2 labeled with two or more luminescent reagents with different luminescent wavelength ranges by using optical interference filters with high wavelength range selectivity. The sample 2 labeled with luminescent reagents is carried on a substrate 1. The light emanating from the luminescent reagents labeling the sample 2 is collected by a condenser lens 3, then transmitted through an optical filter 4, and focused by a convergence lens 5 to a photomultiplier 6 to be detected. The detected signal from the photomultiplier 6 is amplified by an amplifier 7, converted into a digital signal by an A/D converter 8, and processed with a data processor 9.

The optical filter 4 of the device shown in FIG. 1 transmits only a light component within a wavelength range of a luminescent reagent labeling a targeted molecule, and eliminates light components in other wavelength ranges derived from the other luminescent reagents. For sample 2 containing molecules labeled with two or more luminescent reagents with different wavelengths, each molecule may be separately detected by changing the optical filter 4 that allows transmission of light emanated from the luminescent reagent to be detected.

However, the wavelength ranges of luminescent reagents that are actually used often overlap each other. Particularly, when a plurality of (three or more) luminescent reagents are used, it is difficult to select a combination of luminescent reagents such that it does not cause overlapping of their wavelength ranges.

FIG. 2 is a diagram showing wavelength patterns of luminescent light obtained when three types of fluorescent dyes (i.e., fluorescein 14, TMR (carboxy-tetramethyl-rhodamine) 15 and CXR (carboxy-X-rhodamine) 16) are excited with excitation light 13 of 532 nm. The horizontal axis 11 represents wavelength which becomes longer towards right while the vertical axis 12 represents luminous intensity. Generally, when a plurality of luminescent reagents are used as labels, their wavelength ranges overlap as shown in FIG. 2. Thus, even if an optical filter is used for the purpose of obtaining only the light component from the luminescent reagent of interest, light components from other luminescent reagents may leak and pass through the optical filter.

FIG. 3 is the same diagram as that shown in FIG. 2 showing wavelength patterns of luminescent light obtained when the above-mentioned three types of fluorescent dyes are excited with excitation light 13 (532 nm). For example, when an optical filter that transmits light in a wavelength range 17 shown in FIG. 3 is used in a detection system to obtain a light component 16 emanated from the fluorescent dye CXR (hereinafter, referred to as "CXR light component"), a light component 15 emanated from the fluorescent dye TMR (hereinafter, referred to as "TMR light component") partially overlaps the wavelength range 17 as leakage 18 of the light component 15 through the optical filter for detecting the light component 16. The leakage of a light component of a luminescent reagent other than the luminescent reagent of interest causes detection of a band that is absent in one-dimensional electrophoresis, or detection of a band intensity greater than the band intensity originally obtained in one-dimensional electrophoresis.

FIG. 4 is a diagram illustrating that a measured waveform is deformed due to a leak of an irrelevant light component. Due to the leak of the TMR light component, as shown in FIG. 4, the waveform (electrophoresis pattern) 43 of the CXR-labeled molecule obtained by using the optical filter for extracting CXR light component is deformed from a waveform 41 obtained by one-dimensional electrophoresis of the CXR-labeled molecule. Suppose that the waveform pattern 41 of the CXR-labeled molecule obtained by one-dimensional electrophoresis has two peaks 44 and 45, and the waveform pattern 42 of the TMR-labeled molecule has two peaks 46 and 47. If the TMR light component leaks through the optical filter for extracting CXR light component, the detected electrophoresis pattern is influenced as shown in FIG. 4. Where the molecular weight of the CXR-labeled molecule approximates the molecular weight of the TMR-labeled molecule, the peaks obtained by electrophoresis of both molecules by using the optical filter for detecting CXR overlap each other (peaks 45 and 46) and the electrophoresis pattern 43 gives a peak 48 which is greater than its actual peak 45. Where the TMR-labeled molecule is present and the CXR-labeled molecule is absent, a peak 49 appears on the electrophoresis pattern 43 as influenced by the leakage of light component at peak 47 where there should be no peak.

Such misdetection caused by the leakage of light component emanated from a luminescent reagent other than the luminescent reagent of interest is conventionally corrected by software means. Such software calculates the leakage value, and subtracts that value from the actually measured value. First, positions where or time when a molecule labeled with a luminescent reagent A is solely present are empirically predetermined. Then, values at these positions or time as measured with an optical filter a that transmits light emanated from luminescent reagent A and values at the same positions or time as measured with an optical filter b that is not intended to transmit light emanated from the luminescent reagent A are determined. Based on these values, a leakage rate $R_{ab}$ of the light component emanated from the luminescent reagent A leaking through the optical filter b is calculated. The leakage values at the predetermined points are determined based on the value measured with the optical filter a and the leakage rate $R_{ab}$. Each leakage value is then subtracted from the value measured at the same point with the optical filter b, thereby eliminating the influence of the leak of the light component from the luminescent reagent A through the optical filter b.

Hereinafter, the process will be described in more detail with reference to FIGS. 5 and 6A–6C. Molecules 53 and 54 are labeled with luminescent reagents A and B, respectively, the luminescent reagents emitting light having different but partially overlapped wavelength ranges. Then, the molecules 53 and 54 are simultaneously but separately subjected to one-dimensional electrophoreses. FIG. 5 is a diagram showing waveforms 51 and 52 measured with the optical filters a and b for detecting light components from luminescent reagents A and B, respectively. The optical filters a and b have selectivity towards the wavelength ranges of the luminescent reagents A and B, respectively. Provided that the molecule 53 labeled with the luminescent reagent A is not detected at the same time as the molecule 54 labeled with the luminescent reagent B, the molecule 53 is detected with the optical filters a and b as a true peak 55 and as a leakage peak 56, respectively. Provided that the molecule 54 labeled with the luminescent reagent B is not detected at the same time as the molecule 53 labeled with the luminescent reagent A, the molecule 54 is detected with the optical filters a and b as a leakage peak 57 and a true peak 58, respectively.

With regard to the molecule 53 labeled with the luminescent reagent A, a leakage rate $R_{ab}$ of the light component from the luminescent reagent A leaking through the optical filter b is determined as a ratio of a peak component 62 (a volume of measured value exceeding a background value 59 measured with the optical filter a) of peak 56 to a peak component 61 (a volume of measured value exceeding a background value 60 measured with the optical filter b) of peak 55. With regard to the molecule 54 labeled with the luminescent reagent B, the rate of the light component from the luminescent reagent B leaking through the optical filter a is determined as a ratio of a peak component 63 (a volume of measured value exceeding a background value 60 measured with the optical filter a) of peak 58 to a peak component 64 (a volume of measured value exceeding a background value 59 measured with the optical filter a) of a peak 57.

Conventionally, in a software developed for the purpose of calculating the leakage rate by means of user interface, the measured peaks are confirmed on a computer display, and a peak area is selected by the user with a pointing device.

FIGS. 6A–6C are diagrams for illustrating how the background value in the selected peak area is determined by the software. The true peak 61 on the waveform 51 (FIG. 5) as measured with the filter a corresponds to peak 71 in FIG. 6A.

As shown in FIG. 6A, for the peak 71 that is represented as a waveform or as a two-dimensional image on a computer display a peak area 74 is determined by selecting the beginning point 72 and the ending point 73 with the pointing device. The peak area 74 is expanded as shown in FIG. 6B for empirically determined widths 75 and 76, thereby determining an expanded peak area 77 for calculating the background value 59 for the optical filter a.

As shown in FIG. 6C, a set of elements of the values in the expanded peak area 77 measured with the optical filter a are converted into a histogram so that the set of elements are distributed based on their values. The resulting histogram will give an elevation 79 consisting of background values and an elevation 78 consisting of peak values. Since the background elevation 79 made up of lower values forms a relatively clear peak, a peak 80 of the elevation consisting of the lower measured values in the histogram is referred to as a background value $B_a$ of the values measured with the optical filter a. Similarly, a set of elements of the values in the expanded peak area 77 measured with the optical filter b are converted into a histogram, and a peak of the elevation consisting of lower measured values in the histogram is referred to as a background value $B_b$ of the values measured with the optical filter b.

Then, the true peak component 61 (FIG. 5) is calculated by subtracting the background value $B_a$ in the selected peak area 74 obtained above (FIG. 6A) from the value measured with the optical filter a in the same area. The leakage peak component 62 (FIG. 5) is calculated by subtracting the background value $B_b$ in the peak area 74 obtained above from the value measured with the optical filter b in the same area. The thus-obtained leakage peak component 62 is divided by the true peak component 61, thereby obtaining leakage rate $R_{ab}$ of light component generated by luminescent reagent A passing through the optical filter b. The leakage rate $R_{ba}$ of light component generated by luminescent reagent B passing through the optical filter a is also obtained in a similar manner.

The thus-obtained background values $B_a$ and $B_b$ and the leakage rates $R_{ab}$ and $R_{ba}$ are applied to the following Equations (1) and (2) below based on value 51 ($P_a$) measured with the optical filter a and value 52 ($P_b$) measured with the optical filter b, thereby obtaining values $T_a$ and $T_b$ that are excluded of light component leakage caused by luminescent reagents B and A.

$$P_a = (T_a - B_a) + (T_b - B_b) \times R_{ba} + B_a \quad (1)$$

$$P_b = (T_a - B_a) \times R_{ab} + (T_b - B_b) + B_b \quad (2)$$

Background values and leakage rates may also be determined for the case where three or more luminescent reagents and optical filters corresponding thereto are used for the detection. First, two luminescent reagents having the greatest wavelength range overlap area are chosen. Then, using Equations (1) and (2) above, the light component leakage caused by these luminescent reagents is excluded from the measured value. Among other luminescent reagents, one luminescent reagent is chosen which has the greatest wavelength range overlap area with the wavelength range of one of the first two luminescent reagents. Again, using Equations (1) and (2) above, the light component leakage caused by this luminescent reagent is excluded from the measured value. The once-excluded light component leakage $T_a$ or $T_b$ caused by the once-processed luminescent reagent is replaced with $P_a$ or $P_b$ upon the second calculation.

According to such conventional method, the selection of the locations of the true peak to be detected and the selection of the peak areas thereof require clear understanding of the method and skill to use the software. Moreover, in order to obtain uniform results, the user has to be skilled in such experiment so that appropriate background values and leakage rates are always obtained. The background values and leakage rates are highly dependent on the selection of the locations of the true peak to be detected and the selection of peak areas thereof. This has been a problem, for example, in forensic identification where multi-luminescent reagent color separation is utilized as an objective measurement. The conventional method that requires manipulation of the user upon selections of the peaks and the peak areas prevented complete automation of the system of multi-luminescent reagent color separation including the use of the measured results.

The present invention aims at solving such problem and provides a method for automatically obtaining precise background value and leakage rate in color separation and detection thereof using multiple luminescent reagents.

In order to accomplish the above-mentioned aim, the electrophoreosis method of the invention employs a known sample (marker sample) labeled with the same luminescent reagents as the luminescent reagents used for labeling a sample to be subjected to separation measurement. The marker sample and the test sample are simultaneously separated and measured by electrophoresis with a separation device under the same conditions. Since the marker sample can easily be identified from the measured result, a precise background value of the measured value can be calculated. The use of the marker sample allows calculation of precise leakage rate of a light component from a luminescent reagent other than the luminescent reagent of interest. According to the present invention, the background value and the leakage rate of the marker sample upon electrophoresis band measurement can automatically be calculated, and also the leakage light component is automatically subtracted from the measured value.

SUMMARY OF THE INVENTION

The electrophoresis method of the invention includes simultaneously electrophoresing a test sample containing a plurality of molecules labeled with a plurality of luminescent reagents and a marker sample containing a plurality of molecules with known molecular weights labeled with the same plurality of luminescent reagents.

Upon such method, a light component emanated from a first luminescent reagent labeling a marker molecule is measured, by using a first optical filter for separating and detecting the light component from the first luminescent reagent, and by using a second optical filter for separating and detecting a light component from a second luminescent reagent, the results being compared with each other, thereby obtaining a leakage rate of the light component from the first luminescent reagent leaking through the second optical filter. This leakage rate is used to correct the measured values of the light components from the respective luminescent reagents.

The plurality of molecules contained in the marker sample are assigned, based on their molecular weights, to a plurality of bands formed by electrophoresis of the marker molecules.

To obtain the leakage rate, peak areas are subtracted from a waveform measured along the electrophoresis distance of the marker sample, and the obtained value is averaged to be used as a background value.

The marker sample of the invention includes various types of molecules having different molecular weights, and various types of luminescent reagents, wherein molecules of the same molecular weights are labeled with the same luminescent reagent.

The marker sample of the invention includes a plurality of marker groups including various types of molecules having different molecular weights, wherein molecules belonging to the same marker group are labeled with the same luminescent reagent, and molecules belonging to different marker groups are labeled with different luminescent reagents. The marker sample of the invention also includes various types of substances such that they are separated at different locations without overlapping each other upon electrophoresis, wherein the various types of substances are grouped into a plurality of groups, and substances belonging to the same group are labeled with the same luminescent reagent, and substances belonging to different groups are labeled with different luminescent reagents.

An electrophoresis device of the invention includes a test sample electrophoresis section where a test sample containing molecules labeled with a plurality of luminescent reagents is electrophoresed and a marker sample electrophoresis section where the above-described marker sample containing molecules labeled with the same plurality of luminescent reagents is electrophoresed. This electrophoresis device may be a slab gel one-dimensional electrophoresis device, a slab gel two-dimensional device, or a a capillary electrophoresis device.

This specification includes all or part of the contents as disclosed in the specification and/or drawings of Japanese Patent Application No. 10-345476, which is a priority document of the present application.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 6A to 6C are diagrams for illustrating a calculation of a background value;

FIGS. 7A to 7C are diagrams showing results of slab gel electrophoresis of test and marker samples labeled with two types of luminescent reagents which are detected with two types of optical filters;

FIG. 8 is a flowchart for obtaining background values of the light measured with optical filters, and leakage rates of light components from irrelevant luminescent reagents leaking through the optical filters;

FIG. 11 is a view showing an exemplary user interface used in the color separation system employing multi-band color separation marker of the invention.

DETAILED DESCRIPTION OF THE INVENTION

Figure 1:
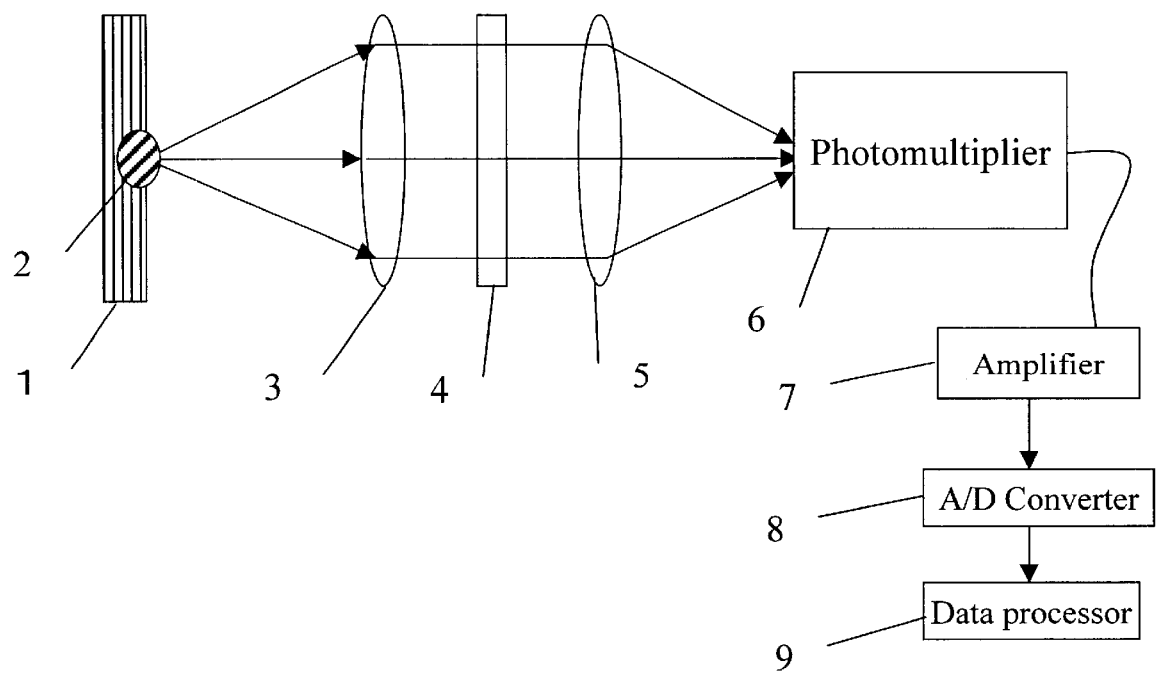
FIG. 1 is a schematic view showing an exemplary device for separating and detecting a sample labeled with two or more luminescent reagents.
Figure 2:
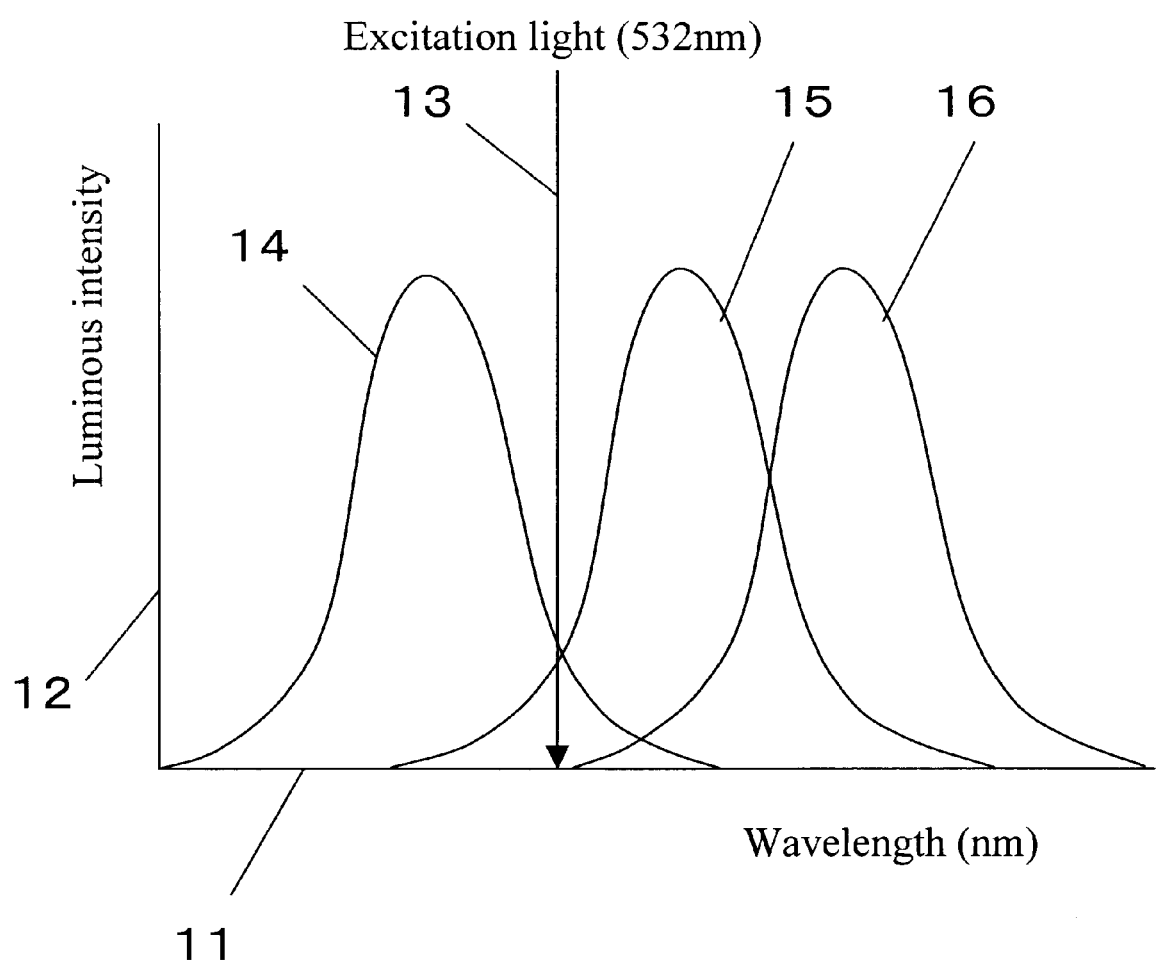
FIG. 2 is a diagram showing an example of overlapping wavelength patterns of three types of fluorescent dyes.
Figure 3:
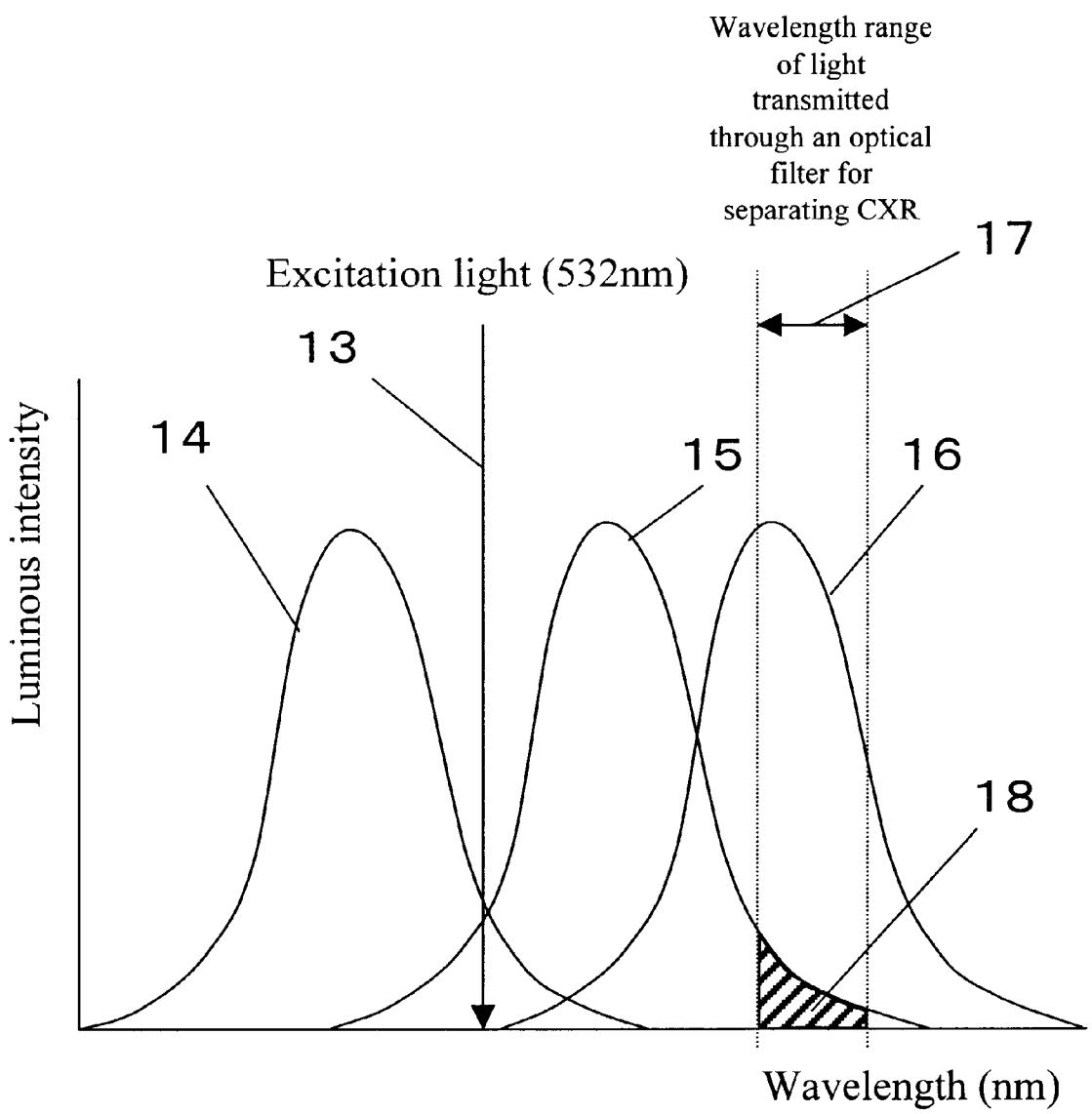
FIG. 3 is a diagram showing an irrelevant light component leaking through an optical filter.
Figure 4:
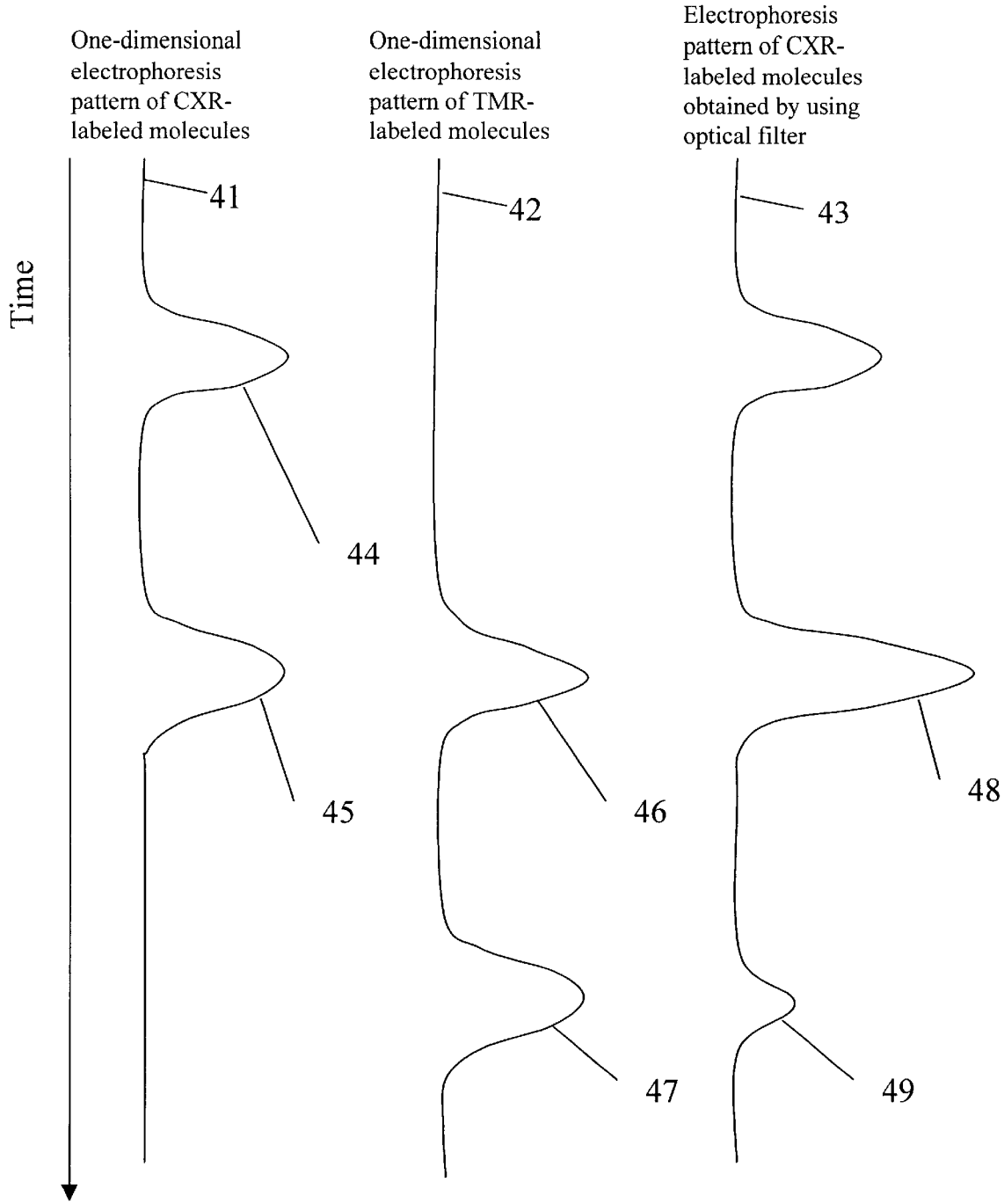
FIG. 4 is a diagram illustrating that a measured waveform is deformed due to a leak of an irrelevant light component.
Figure 5:
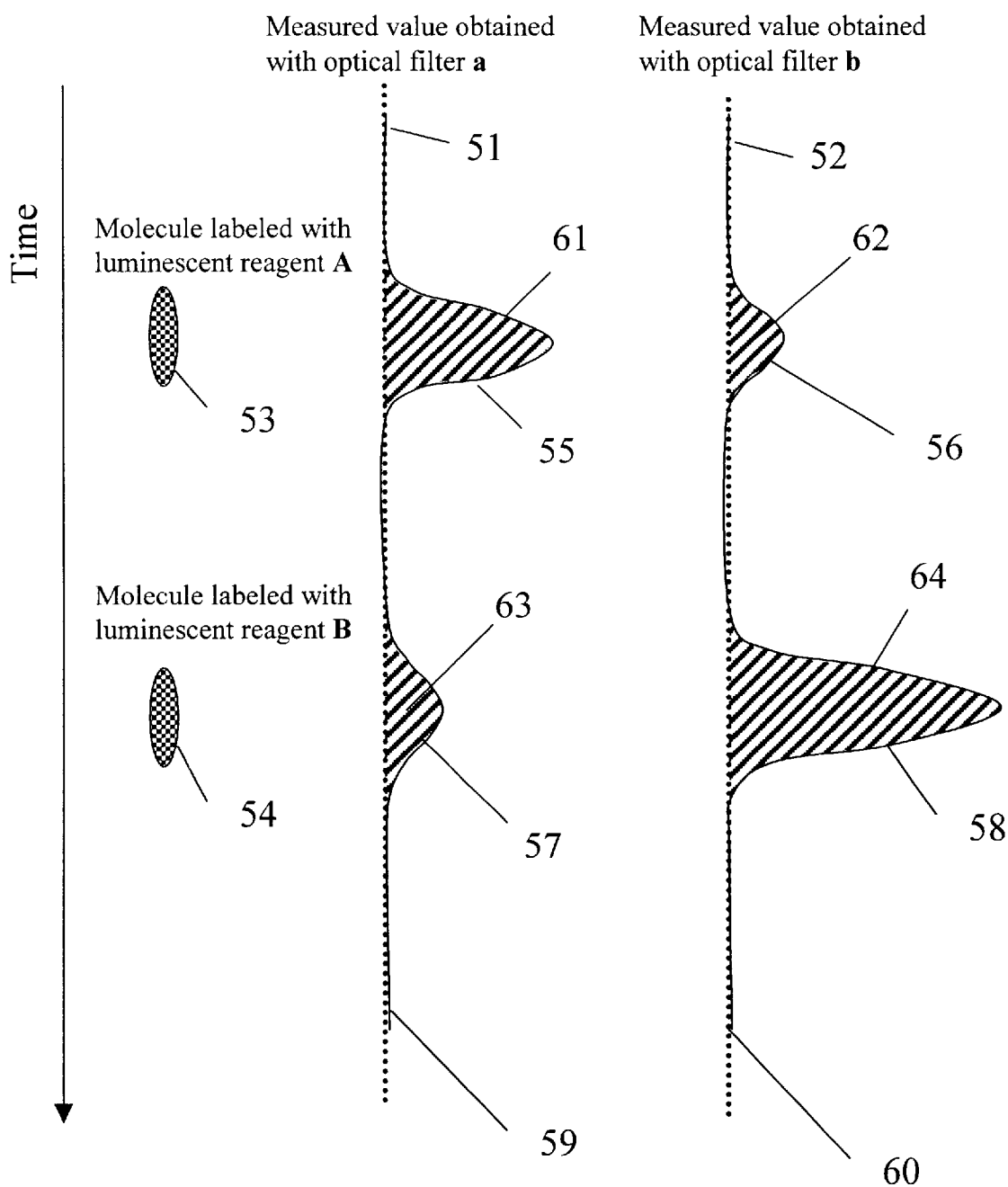
FIG. 5 is a diagram for illustrating a calculation of a leakage rate.

Hereinafter, the present invention will be described in more detail by way of examples with reference to the accompanying drawings.

FIGS. 7A to 7C are diagrams showing results of slab gel electrophoresis of test and marker samples labeled with two types of luminescent reagents. FIG. 7A shows locations of the labeled test and marker samples on the slab gel substrate 101. FIG. 7B shows the results obtained by measuring the electrophoresis substrate 101 shown in FIG. 7A via an optical filter a. FIG. 7C shows the results obtained by measuring the electrophoresis substrate 101 shown in FIG. 7A via an optical filter b.

Referring to FIG. 7A, a gel substrate 101 is provided with a marker sample lane 102 and a test sample lane 103. On the marker sample lane 102, the marker sample is separated into marker molecules A (104) labeled with luminescent reagent A and marker molecules B (105) labeled with luminescent reagent B. On the test sample lane 103, the test sample is separated into a test molecule A (106) labeled with luminescent reagent A and a test molecule B (107) labeled with luminescent reagent B.

When the substrate 101 is visualized via the optical filter a, a substrate image 108 shown in FIG. 7B is obtained. In an area corresponding to the marker sample lane 102, light components 109 from the marker molecules A labeled with luminescent reagent A and leak light components 110 from the marker molecules B labeled with luminescent reagent B appear. In an area corresponding to the test sample lane 103, a light component 111 from the test molecule A labeled with luminescent reagent A and a leak light component 112 from the test molecule B labeled with luminescent reagent B appear. A waveform 113 shown on the left to the visualized substrate image 108 represents the values of the marker sample lane measured with the optical filter a.

Similarly, when the substrate 101 is visualized via the optical filter b, a substrate image 114 shown in FIG. 7C is obtained. In an area corresponding to the marker sample lane 102, leak light components 115 from the marker molecules A labeled with luminescent reagent A and light components 116 from the marker molecules B labeled with luminescent reagent B appear. In an area corresponding to the test sample lane 103, a leak light component 117 from the test molecule A labeled with luminescent reagent A and a light component 118 from the test molecule B labeled with luminescent reagent B appear. A waveform 119 shown on the left to the visualized substrate image 114 represents the values of the marker sample lane measured with the optical filter b.

The marker sample A is selected such that it is suitably separated along the marker lane 102 by electrophoresis. Herein, the marker sample A labeled with luminescent reagent A consists of four marker molecules A with known molecular weights. The marker sample B consists of four marker molecules B labeled with luminescent reagent B and having known molecular weights whose migration distances do not overlap the migration distances of the marker molecules A. The marker sample B is selected such that it is suitably separated along the marker lane 102 by electrophoresis. All marker molecules electrophoresed along the marker lane 102 are selected such that they have known molecular weights whose peaks appear within the electrophoresis range.

The waveforms 113 and 119 (FIGS. 7B and 7C) of the marker lane are obtained by averaging the measured values in horizontal directions of the marker lane along the distance of electrophoresis in the vertical direction of the marker lane.

FIG. 8 is a flowchart for obtaining, based on the measured values 113 and 119 (FIGS. 7B and 7C) of the marker sample, background values of the light measured with the optical filters a and b, a leakage rate of a light component from luminescent reagent A leaking through the optical filter b, and a leakage rate of a light component from luminescent reagent B leaking through the optical filter a.

Figure 9:
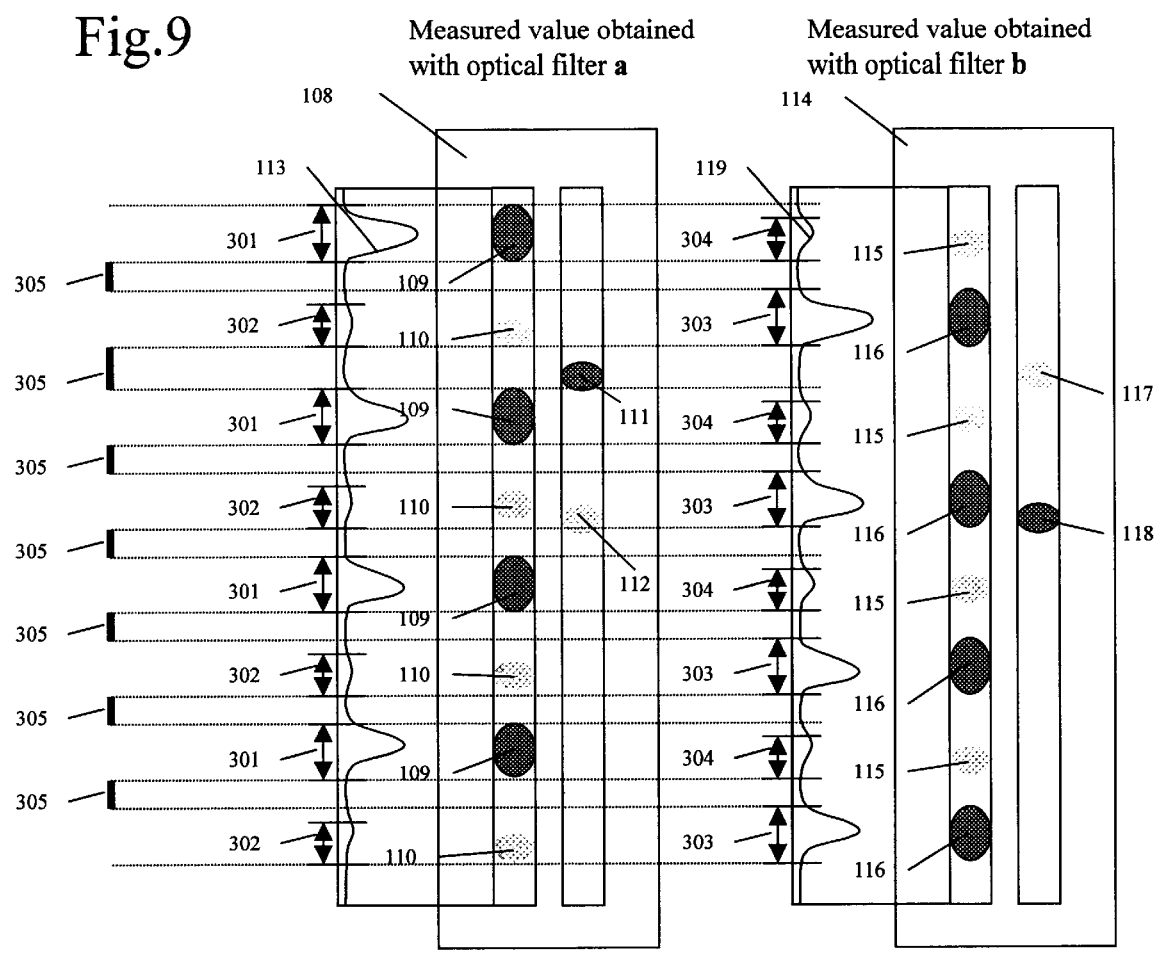
FIG. 9 is a diagram for illustrating calculations of the background value and the leakage rate.

In FIG. 9, ranges 305 are shown which are used for calculating background values, and which are obtained from peak areas that are determined by automatic peak recognition of the measured waveform obtained with the optical filters a and b. True peaks 301 and leakage peaks 302 are obtained by automatic peak recognition of the waveform 113 obtained with the optical filter a. True peaks 303 and leakage peaks 304 are obtained by automatic peak recognition of the waveform 119 measured with the optical filter b. The ranges 305 that remain after excluding the true peaks 301 and. 303 and leakage peaks 302 and 304 are used for calculating the background values.

Figure 10:
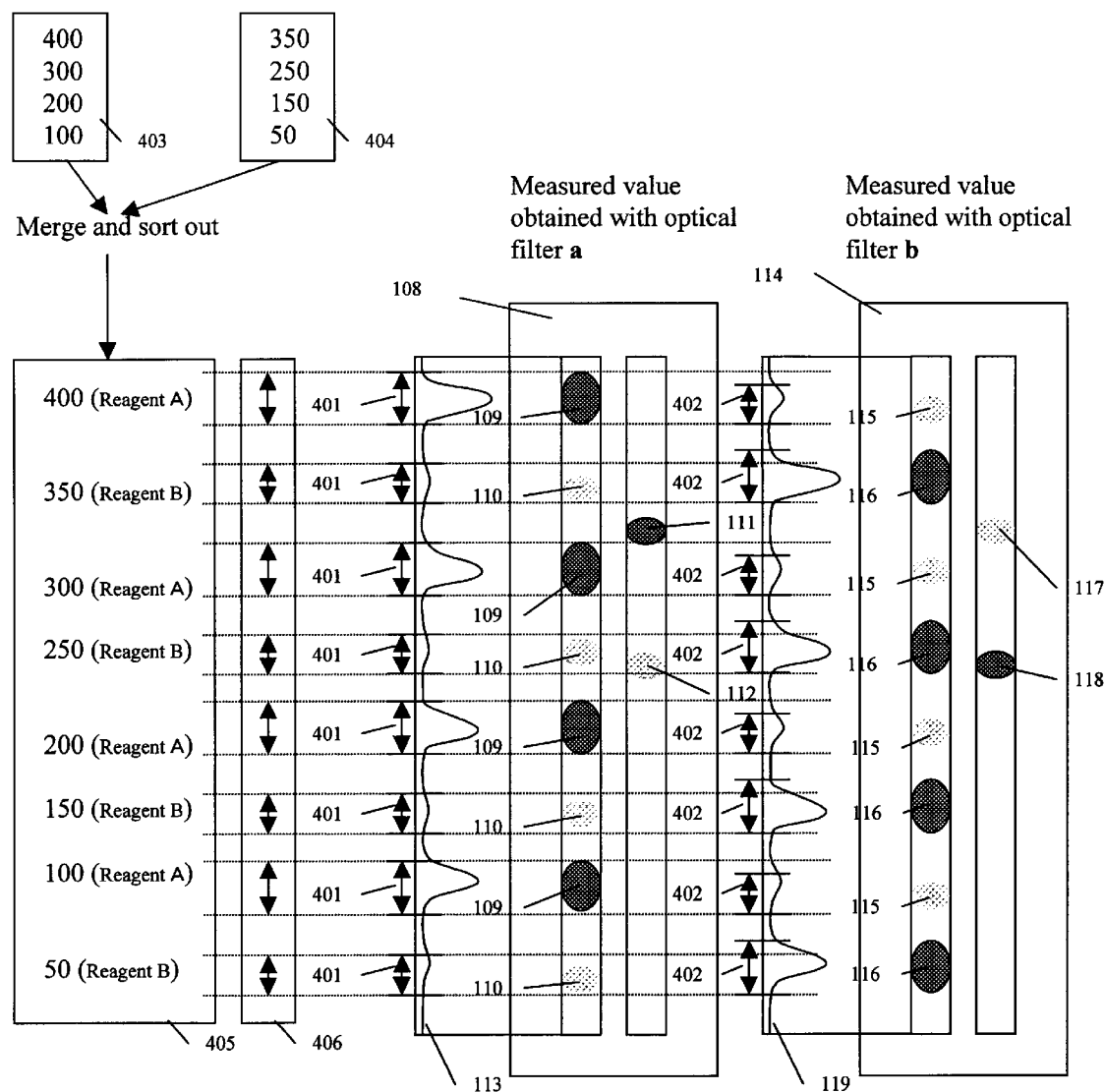
FIG. 10 is a diagram showing how the marker sample information along the marker lane and the peak information obtained from the measured wavelength are assigned to each other.

FIG. 10 is a diagram showing how the marker sample information along the marker lane and the peak information obtained from the measured wavelength are assigned to each other. A set of the four molecules (markers) 403 with different molecular weights labeled with luminescent reagent A are merged with a set of the four molecules (markers) 404 with different molecular weights labeled with luminescent reagent B. The set of merged markers 405 are then sorted out so as to assign to the peaks 406 obtained through automatic peak recognition of the measured waveforms. By doing so, the molecular weights of the marker molecules forming the respective peaks of the measured waveforms and the types of the luminescent reagent (either luminescent reagent A or B) labeling that respective markers can be determined.

FIG. 11 is a view showing an exemplary user interface used in the color separation system employing multi-band color separation marker of the invention. For setting and confirming color separation parameters for determining which peaks on the marker lane correspond to which luminescent dyes, the user interface is provided with an image information displaying section 921 for displaying the image to be detected and for displaying the pixel values of the image as a graph, and a band parameter setting section 922 for actually setting the band parameters. The user interface is also provided with a template button 901 for saving the setting information as a typical setting (template) with a desired name and for loading the saved template to be reused, a template name displaying section 902 for displaying the name designated for the loaded setting template, and a pull-down menu 903 for selecting the lane to be processed.

The image information displaying section 921 consists of a lane displaying section 904 for displaying the image of the selected lane, a lane waveform displaying section 905 for displaying, in correspondence with the image of the lane displaying section 904, waveform graphs representing a sum of the pixel values on the same Y-axis coordinate of each channel measured with each optical filter, and a band area displaying section 906 for displaying the band areas that are automatically recognized for each channel based on the lane waveforms. Zones that are not recognized as a band area of any of the channels are considered as background areas 907 which are shown with meshes. The scale of the image may be selected from a scale list box 908.

The information of all band areas that are automatically recognized for each channel is set in a band parameter setting section 922 by clicking a band area information copy button 909. The information of the set values may be changed with a color selection button 910. The band parameter setting section 922 is provided with a original channel of band information displaying section 911 for displaying colors assigned to the original channel of bands in order, a recognized band information displaying section 912 for indicating the numerical references of the band displayed on the original channel of band information displaying section 911 referring to the numerical references indicated in the image information displaying section 921, and a status displaying section 913 for displaying exceptional conditions of the leaking band information. Other information such as a band area margin and a background margin may be set in a window that opens by clicking a detail parameter setting button 914.

The status displaying section 913 displays information such as "Overlap", "None", "Not band", and "Skip" which are input by clicking the button, if necessary. "Overlap" and "None" are used upon making a template, while "Not band" and "Skip" are used upon utilizing the template information. "Overlap" is used to exclude a recognized band from the leakage rate calculation, for example, when sequential bands are recognized as a single band. The "Overlap" information is saved in the template information. "None" is used when a non-existing band is recognized. The "None" information is not saved in the template information. "Not band" is used when a mis-recognized band is present in the loaded template. By displaying "Not band", the mis-recognized band can be excluded upon the leakage rate calculation. "Skip" is used when a band in the loaded template does not exist. By displaying "Skip", the band on the template is skipped and is not used for the leakage rate calculation.

Hereinafter, a method of the present invention for calculating the background values, and the leakage rates of light components emanated from irrelevant luminescent reagents that are not intended to be detected will be described with reference to the flow chart shown in FIG. 8. In step 201 shown in FIG. 8, locations of peaks and peak areas are determined according to the shapes of the waveforms 113 and 119 of the marker lanes measured with each of the optical filters a and b. For waveform information that have been smoothened based on the empirical value depending on the measured information, the software detects the leading edge and the falling edge (as a peak area) as well as the peak (as a location of the peak) of each peak component according to the automatic peak recognition program. Since each of the values measured via the optical filters a and b contain light components from a luminescent reagent other than the luminescent reagent of interest, the peak formed by that luminescent reagent is also recognized if the leakage is high. The peak areas detected in step 201 are shown in FIG. 10 as the peak areas 401 and 402 of the waveforms 113 and 119, respectively.

In step 202, the peak areas are determined for all of the peaks and they are sorted out based on the migration distances upon electrophoresis. If the peak areas of different waveforms overlap each other, either one of the peak areas is used assuming that they are either a true peak or a leakage peak of the same marker. The number of the thus-obtained peak areas is consistent with the number of all markers subjected to electrophoresis on the marker lane. The peak locations and the peak areas utilized may either be of a true peak or a leakage peak. Herein, the collection of the peak areas 406 (FIG. 10) is used. At this point, it is impossible to judge which peaks on the waveform are the true peaks and which are the leakage peaks. This is because the device of the invention for detecting light may be provided with a plurality of pairs of photomultiplier 6 (FIG. 1) whose sensitivity may vary.

In step 203, a set of marker molecules with different molecular weights 403 (FIG. 10) labeled with luminescent reagent A and a set of marker molecules with different molecular weights 404 labeled with luminescent reagent B are merged with each other and sorted out based on their molecular weights, thereby obtaining collection 405 of marker molecules.

In subsequence step 204, each of the peak areas 406 determined in step 202 is assigned to each of marker molecules sorted out based on molecular weights in step 203. As a result, the molecular weight of the marker molecule for each peak area can be determined. Moreover, by specifying the luminescent reagent labeling the marker molecules of different molecular weights, each peak can be classified as either a true peak or a leakage peak. This allows automation of selecting the true peaks, which has conventionally been judged by the user based on the measured values.

Since true peaks can be determined for every peaks merged in step 202, the peak locations and the peak areas for the true peaks can be determined. Herein, the peak areas 301 and 303 shown in FIG. 9 are the peak areas of the true peaks.

In step 206, the measured values in areas of the waveforms 113 and 119 other than the peak areas determined in step 205 (i.e., the areas 305 shown in FIG. 9) are averaged. The obtained values are the background values $B_a$ and $B_b$ of the values detected with the optical filters a and b, respectively. It can be appreciated that the values of the areas 305 are not influenced by light components from any reagents. By this process, the background values, which have conventionally been unstable due to man-selection, can be obtained in an objective and reproducible manner based on the waveforms of the marker lanes and the parameters for the automatic peak recognition program.

In the subsequent step 207, volumes are determined for every peak areas determined in step 205 using the background value as the baseline. In step 208, the total of the peak volumes of each luminescent reagent is obtained for each of the waveforms.

In step 209, the total peak volume of the waveform measured with an irrelevant optical filter is divided by the total peak volume of the waveform measured with an optical filter for the target luminescent reagent, thereby obtaining leakage rates $R_{ab}$ and $R_{ba}$. Accordingly, the leakage rate, which is conventionally calculated based on user-selected peaks and peak areas, can be automatically calculated. The method of the invention refers to the measured values at the beginning, intermediate and ending regions of the electrophoresis area, and is capable of calculating leakage rate that is applicable to the whole electrophoresis area.

The background values $B_a$ and $B_b$ upon light detection with the respective optical filters a and b, and the leakage rates $R_{ab}$ and $R_{ba}$ of light components leaking through irrelevant optical filters are applied to the conventional Equations (1) and (2) above, thereby obtaining a value excluded of the light component of the irrelevant luminescent reagent. According to the present invention, the background values upon light detection with the respective optical filters, and the leakage rates of the light component leaking through irrelevant optical filters can objectively and automatically be calculated. Thus, automatic calculation of the measured value excluded of the light component from irrelevant luminescent reagents, objective data analysis using such measured value, and automation of such data analysis are possible.

Figure 12A:
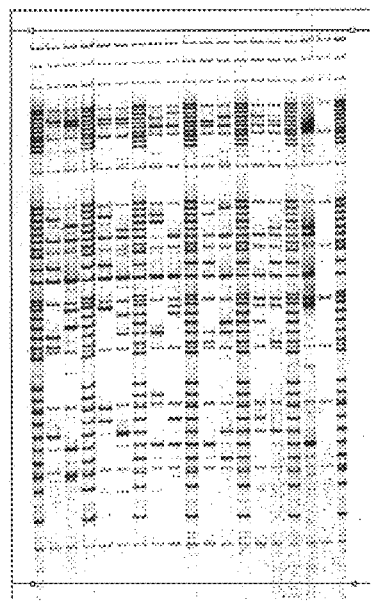
FIGS. 12A to 12C are pictures for illustrating the effectiveness of the invention.
Figure 12B:
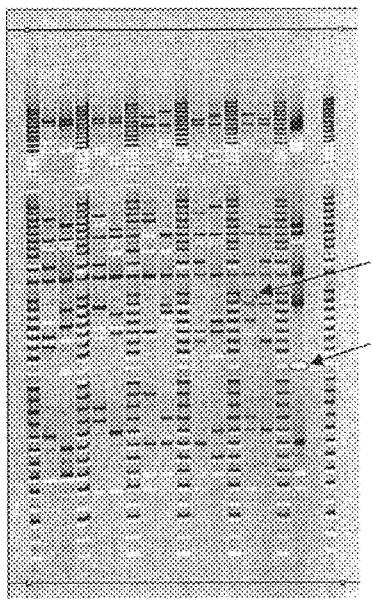
Figure 12C:
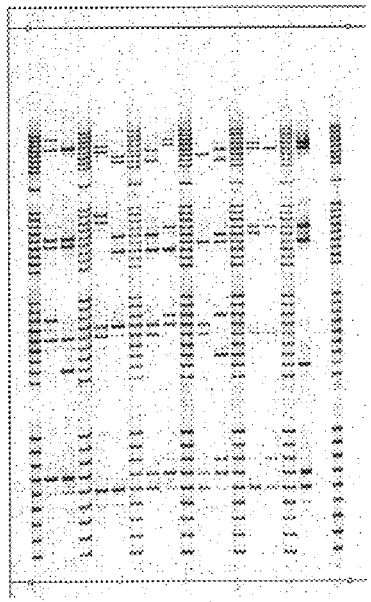

FIGS. 12A to 12C are pictures for illustrating the effectiveness of the invention. Samples containing molecules labeled with three types of fluorescent dyes (i.e., fluorescein, TMR and CXR) were electrophoresed. Three optical filters that specifically transmit light in wavelength ranges of 505 nm, 585 nm and 650 nm for separating light components from fluorescein, TMR and CXR, respectively, were used for detecting the separation, and three images were obtained. The result was processed to exclude the leak of light components from dyes other than the dye of interest.

FIG. 12A is a picture showing an unprocessed image obtained with the optical filter that specifically transmits light in the wavelength range of 585 nm. FIG. 12B is a picture showing an image obtained by excluding the light component leakage from the image of FIG. 12A using the leakage parameters obtained by a conventional. method. FIG. 12C is a picture showing an image obtained by excluding the light component leakage from the image of FIG. 12A using the leakage parameters obtained by the method of the present invention. Referring to FIG. 12B, the remaining light component from CXR and excessive elimination of light component from fluorescein are indicated with arrows A and B, respectively. Such remainder or excessive elimination of the light component was not found in the image shown in FIG. 11C, proving the effectiveness of the method of the present invention.

According to the present invention, when a plurality of luminescent reagents with different wavelengths are separated and detected by using corresponding optical filters, the leakage of a light component through an optical filter that is not intended for that light component is automatically calculated based on objective observation data, and gives results eliminated of the leakage.

All publications, including patent and patent application cited herein are incorporated herein by reference in their entirety.

What is claimed is:

1. An electrophoresis method, comprising simultaneously electrophoresing a test sample comprising a plurality of molecules labeled with a plurality of luminescent reagents and a marker sample comprising a plurality of molecules with known molecular weights labeled with the same plurality of luminescent reagents, wherein a light component emanated from a first luminescent reagent labeling a marker molecule is measured by using a first optical filter for separating and detecting the light component from the first luminescent reagent and by using a second optical filter for separating and detecting a light component from a second luminescent reagent, the results being compared with each other, thereby obtaining a leakage rate of the light component from the first luminescent reagent leaking through the second optical filter.

2. The electrophoresis method of claim 1, wherein the leakage rate is used to correct the measured values of the light components from the respective luminescent reagents.

3. The electrophoresis method of claim 1, wherein the plurality of molecules contained in the marker sample are assigned, based on their molecular weights, to a plurality of bands formed by electrophoresis of the marker molecules.

4. The electrophoresis method of claim 1, wherein peak areas are subtracted from a waveform measured along the electrophoresis distance of the marker sample, and the obtained value is averaged to be used as a background value.

5. The electrophoresis method of claim 1, wherein the marker sample comprises a plurality of various types of substances such that the substances when electrophoresed simultaneously in an electrophoretic gel are separated in the electrophoretic gel at different locations without overlapping each other, wherein the various types of substances are grouped into a plurality of groups, and substances belonging to the same group are labeled with the same luminescent reagent, and substances belonging to different groups are labeled with different luminescent reagents.

6. The electrophoresis method of claim 1, wherein the marker sample comprises a plurality of types of molecules having different molecular weights, and a plurality of types of luminescent reagents, wherein molecules having the same molecular weights are labeled with the same luminescent reagent.

7. The electrophoresis method of claim 1, wherein the marker sample comprises a plurality of marker groups comprising a plurality of various types of molecules having different molecular weights, wherein molecules belonging to the same marker group are labeled with the same luminescent reagent, and molecules belonging to different marker groups are labeled with different luminescent reagents.

8. The electrophoresis method of claim 1, wherein a luminescent reagent is selected from the group consisting of a fluorescein, a carboxy-tetramethyl-rhodamine and a carboxy-X-rhodamine.

9. The electrophoresis method of claim 1, wherein a leakage rate of a light component is determined using an equation comprising $$P_a = (T_a - B_a) + (T_b - B_b) \times R_{ba} + B_a$$

wherein the leakage rate is $R_{ba}$, the background values are $B_a$ and $B_b$, and $T_a$ and $T_b$ are light component leakage values.

10. The electrophoresis method of claim 1, wherein a leakage rate of a light component is determined using an equation comprising $$P_b = (T_a - B_a) \times R_{ab} + (T_b - B_b) + B_b$$

wherein the leakage rate is $R_{ab}$, the background values are $B_a$ and $B_b$, and $T_a$ and $T_b$ are light component leakage values.

11. The electrophoresis method of claim 1, further comprising use of a user interface.

12. The electrophoresis method of claim 1, wherein the user interface comprises an image information displaying section for displaying an image and displaying pixel values of an image as a graph.

* * * * *